United States Patent [19]
Beck

[11] 3,948,957
[45] Apr. 6, 1976

[54] 3-AZIDO-2,6-DINITROANILINES

[75] Inventor: James R. Beck, Indianapolis, Ind.

[73] Assignee: Eli Lilly and Company, Indianapolis, Ind.

[22] Filed: June 23, 1975

[21] Appl. No.: 589,314

[52] U.S. Cl. .................... 260/349; 71/121; 424/226
[51] Int. Cl.² ....................................... C07C 117/00
[58] Field of Search ..................................... 260/349

[56] References Cited
UNITED STATES PATENTS
3,770,779  11/1973  Kiehs .................................. 260/349

*Primary Examiner*—Lewis Gotts
*Assistant Examiner*—Cary Owens
*Attorney, Agent, or Firm*—Leroy Whitaker; Everet F. Smith

[57] ABSTRACT

A new class of 2,6-dinitroanilines has been prepared. The new compounds possess an azido group in the 3-position. Such compounds possess herbicidal activity and also activity against *Plasmopara viticola*.

7 Claims, No Drawings

3-AZIDO-2,6-DINITROANILINES

BACKGROUND OF THE INVENTION

1. Field of the Invention

This invention relates to new chemical compounds. More particularly, this invention relates to 3-azido-2,6-dinitroanilines.

2. Description of the Prior Art

Various 2,6-dinitroanilines have been described in the chemical literature. Hantzsch, *Deutsche Chemische Gesellschaft Berichte*, 43, 1662-1685 (1910) discloses N,N-dipropyl-4-methyl-2,6-dinitroaniline and N,N-dimethyl-4-methyl-2,6-dinitroaniline. Joshi et al., C.A. 28, 469 (1934) disclose N,N-dimethyl-4-iodo-2,6-dinitroaniline, N,N-dimethyl-4-bromo-2,6-dinitroaniline, 4-iodo-2,6-dinitrophenylpiperidine, and 4-bromo-2,6-dinitrophenylpiperidine. Borsche et al., C.A. 5, 2079 (1911) disclose 2,6-dinitrophenylpiperidine. Daudt et al., U.S. Pat. No. 2,212,825, disclose a number of 2,6-dinitroanilines anilines bearing a trifluoromethyl group in the 4-position.

The utility of 2,6-dinitroanilines in agriculture was first disclosed in Soper U.S. Pat. Nos. 3,111,403; 3,257,190; 3,332,769; and 3,367,949. Soper disclosed such compounds to possess herbicidal activity, notably preemergent herbicidal activity. Following Soper, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939.

SUMMARY OF THE INVENTION

I have now discovered a new group of 3-azido-2,6-dinitroanilines having the formula:

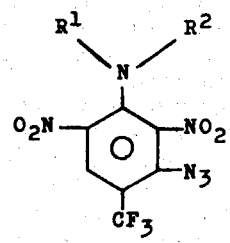

wherein
R[1] is hydrogen, $C_1$–$C_5$ nontertiary alkyl, $C_3$–$C_4$ alkenyl, chloro $C_2$–$C_3$ alkyl, chloro $C_3$–$C_4$ alkenyl or $C_4$–$C_7$ cycloalkylalkyl;
when R[1] is hydrogen, R[2] is $C_1$–$C_7$ nontertiary alkyl, $N(R^3)_2$, $C_3$–$C_4$ alkenyl, phenyl, chlorophenyl or N-methyl-2-propionamide;
when R[1] is other than hydrogen, R[2] is $C_1$–$C_7$ non-tertiary alkyl, chloro $C_2$–$C_3$ alkyl, $C_3$–$C_4$ alkenyl, chloro $C_3$–$C_4$ alkenyl or $C_4$–$C_7$ cycloalkylalkyl;
each R[3] is $C_1$–$C_3$ alkyl.

My new compounds possess herbicidal activity and fungicidal activity against the causative organism of grape downy mildew.

DESCRIPTION OF THE PREFERRED EMBODIMENT

In the above description of my compounds, all of the terms employed have the meanings normally ascribed to them in the chemical art.

The novel 3-azido-2,6-dinitroanilines of my invention are prepared from the corresponding 3-chloro-2,6-dinitroanilines by reaction of the chloro compound with an alkali metal azide such as sodium azide in an inert solvent. The reaction proceeds readily at temperatures within the range of from about 10° to about 50°C., preferably within the range of about 25 to about 30°C. Suitable inert solvents include dimethylformamide, dimethylacetamide, tetrahydrofuran, dimethyl sulfoxide, and the like.

Preferably, an aqueous solution of the alkali metal azide is added dropwise to a stirred solution of the 3-chloro-2,6-dinitroaniline in a solvent, such as dimethylformamide. Stirring of the reaction mixture is continued, preferably at room temperature, for from 30 minutes to 3 hours. Generally, the reaction will be complete in about 1 hour. The product is recovered by pouring the reaction mixture over ice and filtering.

The 3-chloro starting materials for the preparation of the azido compounds of my invention are prepared by reacting the appropriate amine or appropriate hydrazine with 2,4-dichloro-3,5-dinitrobenzotrifluoride as described in U.S. Pat. No. 3,617,252. The amine or hydrazine is chosen to give the desired substitution pattern on the anilino nitrogen of the final product. The amine or hydrazine reacts preferentially with the chlorine atom between the two nitro groups of the 2,4-dichloro-3,5-dinitrobenzotrifluoride to give the 3-chloro-2,6-dinitroaniline starting material for use in preparing the compounds of my invention.

The following examples illustrate the preparation of my novel compounds, but such examples are not to be interpreted as placing any limitation upon the scope of the invention.

EXAMPLE 1

A solution of 2.3 gm. of sodium azide in 15 ml. of water was added dropwise to a solution of 7 gm. of 3-chloro-N,N-dimethyl-2,6-dinitro-4-trifluoromethylaniline in 90 ml. of dimethylformamide at room temperature. The mixture was stirred at room temperature for one hour, poured over ice-water, and filtered to recover 6.9 gm. (94%) of 3-azido-N,N-dimethyl-2,6-dinitro-4-trifluoromethylaniline, m.p. 66°–67°C. The structure was confirmed by the NMR spectrum and elemental analysis.

Calculated: C, 33.76; H, 2.20; N, 26.25; Found: C, 33.98; H, 2.19; N, 26.53.

EXAMPLE 2

A solution of 0.75 gm. of sodium azide in 15 ml. of water was added dropwise to a solution of 3.5 gm. of N-n-butyl-3-chloro-2,6-dinitro-N-ethyl-4-trifluoromethylaniline in 75 ml. of dimethylformamide at room temperature. The mixture was stirred at room temperature for 2 hours and poured over ice-water. The product separated as an oil. The mixture was extracted three times with methylene chloride, the methylene chloride evaporated to dryness, the residue taken up in ether, and the ether solution extracted three times with water. Evaporation of the ether left 3.1 gm. (92%) of 3-azido-N-n-butyl-2,6-dinitro-N-ethyl-4-trifluoromethylaniline as an oil. The structure was confirmed by the NMR spectrum and elemental analysis.

Calculated: C, 41.49; H, 4.02; N, 22.33; Found: C, 41.39; H, 3.89; N, 22.10.

EXAMPLE 3

A solution of 1.0 gm. of sodium azide in 10 ml. of water was added dropwise to a solution of 3.2 gm. of N-(3-chloro-2,6-dinitro-4-trifluoromethylphenyl)-N',N'-dimethylhydrazine in 80 ml. of dimethylformamide at room temperature. The mixture was stirred at room temperature for 1 hour, poured over ice-water, and filtered. The solid product was dried and recrystallized from 2B ethanol to yield 3.1 gm. (93%) of N-(3-azido-2,6-dinitro-4-trifluoromethylphenyl)-N',N'-dimethylhydrazine, m.p. 123°–125°C. The structure was confirmed by the NMR spectrum and elemental analysis.

Calculated: C, 32.25; H, 2.41; N, 29.25; Found: C, 32.21; H, 2.39; N, 29.34.

Following the procedure of one of the above examples, the following additional compounds of my invention were prepared.

| $R^1$ | $R^2$ | Melting Point, °C. |
|---|---|---|
| $C_2H_5$ | $C_2H_5$ | Oil |
| H | $CH(CH_3)C_3H_7$ | 25(Oil) |
| H | $CH(CH_3)C_2H_5$ | 77–78 |
| H | $CH[CH(CH_3)_2]_2$ | Oil |
| H | $CH(C_2H_5)C_3H_7$ | 27–28 |
| H | $CH_3$ | 118–120 |
| $C_2H_5$ | $n$-$C_3H_7$ | Oil |
| H | $4$-$ClC_6H_4$ | 119–121 |
| H | $CH(C_2H_5)_2$ | 77–79 |
| $n$-$C_3H_7$ | $n$-$C_3H_7$ | Oil |
| H | $CH(CH_3)CONHCH_3$ | 163(dec.) |
| H | $n$-$C_3H_7$ | 70–72 |
| $C_2H_5$ | methallyl | 46–48 |

The compounds of this invention are useful as herbicides, especially preemergent herbicides, and in the control of *Plasmopara viticola*, the causative organism of downy mildew of grape. The preferred compounds for herbicidal use are those wherein $R^1$ in the above formula is hydrogen and $R^2$ is a secondary $C_3$–$C_7$ alkyl group or each of $R^1$ and $R^2$ is a $C_2$–$C_4$ nontertiary alkyl group, a $C_3$–$C_4$ alkenyl group, a chloro $C_2$–$C_3$ alkyl group, a chloro $C_3$–$C_4$ alkenyl group, or a cyclopropylmethyl group. Especially preferred as herbicides are those compounds wherein $R^1$ is hydrogen and $R^2$ is 2-butyl, 2-pentyl, or 3-pentyl. Other preferred herbicides are those compounds wherein each of $R^1$ and $R^2$ is ethyl or propyl.

My compounds also have exhibited good activity in the control of grape downy mildew. All of the compounds described above as preferred herbicides are also preferred as fungicides. Additional preferred fungicides are those compounds wherein $R^1$ is hydrogen and $R^2$ is methyl, both $R^1$ and $R^2$ are methyl, $R^1$ is ethyl and $R^2$ is methallyl, and $R^1$ is hydrogen and $R^2$ is dimethylamino.

My compounds are used as herbicides or fungicides in accordance with procedures well known in the agricultural art. For either use, the compounds are preferably employed in liquid, powder, or dust compositions containing one or more of the active compounds. In preparing such compositions, the compounds can be modified with one or more of a plurality of additaments, including organic solvents, petroleum distillates, water, or other liquid carriers, surface active dispersing agents, and finely divided inert solids. In such compositions, the active compound can be present in a concentration from about 2 to about 98% by weight.

In the preparation of dust compositions, the active ingredient can be compounded with any of the finely divided solids, such as pyrophyllite, talc, chalk, gypsum, and the like. In such operations, the finely divided carrier is ground or mixed with the active ingredient or is wet with a solution of the active ingredient in a volatile organic solvent. Similarly, dust compositions containing the active compound can be prepared with various solid surface active dispersing agents, such as fuller's earth, bentonite, attapulgite, and other clays. Depending on proportions of ingredients, these dust compositions may be employed as such or may be diluted with an additional solid surface active dispersing agent or with pyrophyllite, chalk, talc, gypsum, and the like to obtain a composition containing the desired amount of active ingredient. Also, such dust compositions can be dispersed in water with or without the aid of dispersing agents to form liquid sprayable mixtures.

The compounds of this invention or a liquid or dust concentrate composition containing such active compounds can be incorporated in intimate mixture with surface active dispersing agents, such as nonionic emulsifying agents, to form spray compositions. Such compositions may be employed as such or may be dispersed in liquid carriers to form diluted sprays containing the active compound in any desired amount.

Similarly, my compounds can be mixed with a suitable water immiscible organic liquid and a surface active dispersing agent to produce emulsifiable concentrates which can be further diluted with water and/or oil to form spray mixtures in the form of oil-water emulsions. Preferred dispersing agents to be employed in these compositions are oil-soluble and include the nonionic emulsifiers, such as condensation products of alkylene oxides with phenols, sorbitan esters, complex ether alcohols, and the like. Suitable organic liquids which can be employed include petroleum oils and distillates, toluene, and synthetic organic oils. The surface active dispersing agents are usually employed in liquid compositions in the amount of from 0.1 to 20% by weight of the composition.

For herbicidal applications, my compounds are employed at a rate of from about 0.5 to about 10 kg./ha. My compounds are preferably employed as preemergence herbicides and may be sprayed onto the surface of the area to be treated or may be mixed into the soil. The compounds are useful in eliminating undesirable vegetation in areas where crops such as cotton and soybeans are grown.

When employed to control grape downy mildew, my compounds are employed at the rate of 10 gm. to 2 kg. of active ingredient per hectare. The compounds are applied to the foliage of the grape plants as a liquid or dust spray. As is customary in such application, it may be necessary to apply the compounds more than once during the growing season.

In addition to having activity as described above, my compounds are also useful as intermediates in the preparation of herbicides such as those described in U.S. Pat. No. 3,617,252. The conversion of the azido group to an amino group is accomplished by treatment with sodium sulfide in an inert solvent, such as a mixture of ethyl acetate and water.

Caution should be exercised in working with the compounds of this invention since some of them have demonstrated explosive tendencies.

I claim:

1. A compound having the formula:

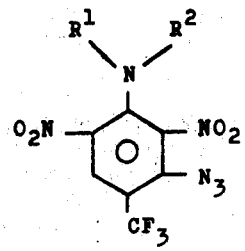

wherein
R$^1$ is hydrogen, C$_1$–C$_5$ nontertiary alkyl, C$_3$–C$_4$ alkenyl, chloro C$_2$–C$_3$ alkyl, chloro C$_3$–C$_4$ alkenyl or C$_4$–C$_7$ cycloalkylalkyl;

when R$^1$ is hydrogen, R$^2$ is C$_1$–C$_7$ nontertiary alkyl, N(R$^3$)$_2$, C$_3$–C$_4$ alkenyl, phenyl, chlorophenyl or N-methyl-2-propionamide;

when R$^1$ is other than hydrogen, R$^2$ is C$_1$–C$_7$ nontertiary alkyl, chloro C$_2$–C$_3$ alkyl, C$_3$–C$_4$ alkenyl, chloro C$_3$–C$_4$ alkenyl or C$_4$–C$_7$ cycloalkylalkyl;

each R$^3$ is C$_1$–C$_3$ alkyl.

2. The compound of claim 1 which is 3-azido-2,6-dinitro-N-(3-pentyl)-4-trifluoromethylaniline.

3. The compound of claim 1 which is 3-azido-2,6-dinitro-N-(2-pentyl)-4-trifluoromethylaniline.

4. The compound of claim 1 which is 3-azido-N-(2-butyl)-2,6-dinitro-4-trifluoromethylaniline.

5. The comound of claim 1 which is 3-azido-2,6-dinitro-N,N-di-n-propyl-4-trifluoromethylaniline.

6. The compound of claim 1 which is 3-azido-N,N-diethyl-2,6-dinitro-4-trifluoromethylaniline.

7. The compound of claim 1 which is 3-azido-2,6-dinitro-N-methyl-4-trifluoromethylaniline.

* * * * *